United States Patent [19]

Weaver

[11] Patent Number: 4,790,314

[45] Date of Patent: Dec. 13, 1988

[54] ORIFICE DILATOR

[76] Inventor: Kenneth Weaver, 311 Princeton Pl., Princeton Rd., Johnson City, Tenn. 37601

[21] Appl. No.: 168,683

[22] Filed: Mar. 16, 1988

[51] Int. Cl.$^4$ .......................................... A61M 29/00
[52] U.S. Cl. ............................... 128/341; 128/303 R; 128/303.11
[58] Field of Search .................. 128/3, 12, 20, 303.11, 128/303 R, 304, 305.3, 341, 343, 345

[56] References Cited

U.S. PATENT DOCUMENTS

| 241,569 | 5/1881 | Stohlmann et al. |
|---|---|---|
| 672,377 | 4/1901 | Kearns . |
| 1,722,893 | 7/1929 | Burnier ............................. 128/345 |
| 2,290,571 | 7/1942 | Peyton . |
| 2,443,207 | 6/1948 | Tedford ............................ 128/345 |
| 3,648,683 | 3/1972 | Brodie . |
| 3,747,603 | 7/1973 | Adler . |
| 3,968,800 | 7/1976 | Vilasi .............................. 128/345 |
| 4,240,412 | 12/1980 | James . |
| 4,624,258 | 11/1986 | Stubbs . |

Primary Examiner—Stephen C. Pellegrino
Assistant Examiner—Colleen Reilly
Attorney, Agent, or Firm—Bell, Seltzer, Park & Gibson

[57] ABSTRACT

A surgical instrument adapted to probe body orifices of different sizes is disclosed. The instrument comprises a post defining a central axis and a plurality of separate probe members mounted in a side-by-side arrangement axially along the post. The probe members rotate freely and individually around the post axis. Each probe member comprises a mounting portion having a transverse opening receiving the post, and an elongate dilator extending radially outwardly from the mounting portion. Each dilator has a size different from that of the other dilators in the instrument. Means are provided for maintaining the axial positioning of the probe members on the post.

9 Claims, 1 Drawing Sheet

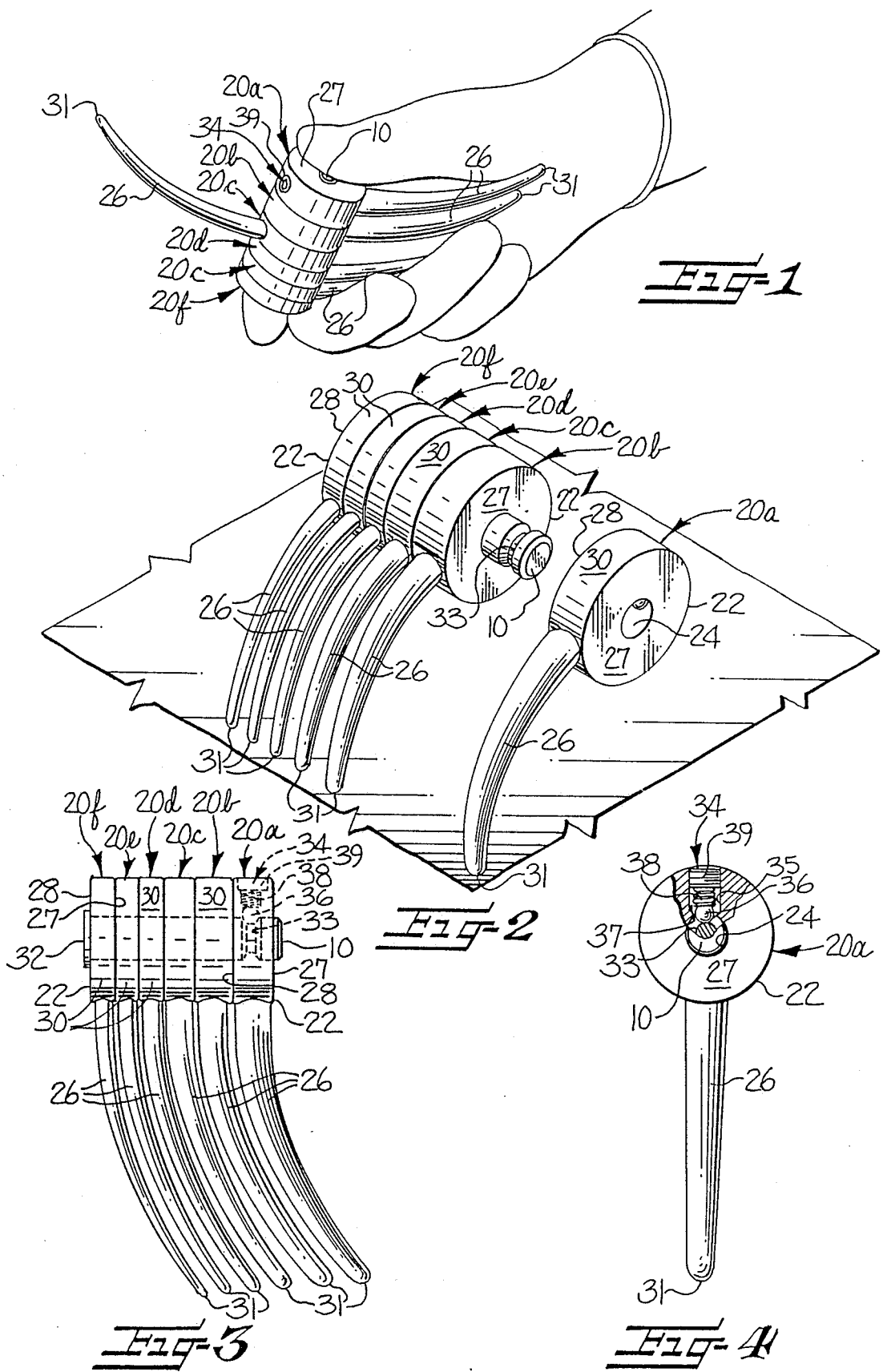

ORIFICE DILATOR

FIELD OF THE INVENTION

This invention relates to surgical instruments generally, and particularly relates to orifice dilators.

BACKGROUND OF THE INVENTION

Orifice dilators are commonly used surgical instruments in a variety of medical procedures. Urethral dilators are used by gynecological urologists and urologists treating female patients. In obstetrics and gynecology, dilation is often a prerequisite for the placement and removal of intrauterine devices, induction of labor, radium placement, drainage of the uterine cavity, endometrial biopsy procedures, uterine curettage, and a variety of other procedures.

In these procedures, dilation should be accomplished gradually. One approach is to construct the dilator of a fiber material which absorbs fluid and expands when placed in a body cavity. This approach is exemplified by the devices disclosed in U.S. Pat. Nos. 4,624,258 to Stubbs and 241,569 to Stohlman et al. Such devices can be used only once, must be carefully sterilized through the entire article, and—because they are fibrous—can be subject t fraying and splintering. Another approach is to use a set of graduated size dilators constructed of surgical steel, as exemplified by U.S. Pat. No. 672,377 to Kearns. A disadvantage of such sets, however, is that the physician must handle a cumbersome number of instruments.

Accordingly, an object of the present invention is to provide a set of surgical dilators which may be easily sterilized and reused.

Another important object of the present invention is to provide a set of surgical dilators which are assembled as a single surgical instrument, and do not require a physician to work with a number of separate instruments to accomplish dilation.

SUMMARY OF THE INVENTION

The foregoing and other objects and advantages of the present invention are achieved by a surgical instrument adapted to probe body orifices of different sizes, as disclosed herein. The instrument comprises a post defining a central axis, and a plurality of separate probe members mounted in a side-by-side arrangement axially along the post, and for independent rotation about said axis. Each of the probe members comprises a mounting portion having a transverse opening receiving the post, and an elongate dilator extending radially outwardly from the mounting portion. Each dilator has a size different from that of the other dilators of the instrument. The probe members are configured so that each may be freely and independently rotated about the axis of the post without interference with other probe members. The instrument includes means for maintaining the axial positioning of the probe members on the post. Probe members having a dilator of a desired size may be selected and rotated to a position where the dilator is separated from the other dilators, to thereby permit the selected dilator to be individually used in probing a body orifice.

DESCRIPTION OF THE DRAWINGS

FIG. 1 is a perspective view of a surgical instrument of the present invention as it may be grasped by a physician, with one of the probe members rotated to a position where the dilator is separated from the other dilators.

FIG. 2 is a perspective view of a surgical instrument of the present invention, with one of the probe members removed from the post.

FIG. 3 is a side view of the instrument shown in FIGS. 1 and 2, showing the means for engaging the annular groove formed in the post.

FIG. 4 is a top plan view of the instrument shown in FIGS. 1 and 2, with portions cut away to show the means for engaging the annular groove formed in the post.

DETAILED DESCRIPTION OF THE PREFERRED EMBODIMENT

A preferred embodiment of the present invention is illustrated in FIGS. 1-4. As illustrated, the surgical instrument comprises a post 10 defining a central axis, and a plurality of separate probe members 20a-20f. Each of the probe members 20a-20f comprises a mounting portion 22 having a transverse opening 24 and an elongate dilator 26 extending radially outwardly from the mounting portion. The device preferably includes at least four of such probe members, and as illustrated, the device includes six probe members. Also, the entire instrument is preferably fabricated from stainless steel, so as to facilitate its sterilization by autoclaving or the like.

The preferred embodiment shown is particularly adapted for use as a urethral dilator. However, it can be adapted to a variety of other uses by those skilled in the art without departing from the spirit of the present invention.

The mounting portions 22 of the probe members are of a disc-like configuration, and include opposite parallel end faces 27,28 which lie in planes which are perpendicular to the axis of the post. Adjacent end faces of adjacent mounting portions are in contact with one another. The mounting portions have cylindrical outer peripheral walls 30 which extend coaxially about said axis of said post, and which are of equal diameter. The thickness of each of said mounting portions between the parallel end faces is at least as great as the maximum diameter of the dilator 26 mounted thereto. In combination with the uniform shaping of the dilators, as explained below, this relation of dilator diameter to probe member thickness permits each of the dilators to be freely and independently rotated about the axis of the post without interference with other probe members.

Each of the dilators 26 is connected to the cylindrical outer peripheral wall 30 of one of the mounting portions. Each dilator is cylindrical and tapers (decreases in diameter) as it extends radially outwardly, and terminates in a blunt point 31. Each dilator 26 is arcuately curved along its length when viewed in a direction perpendicular to the axis of the post 10, as best shown in FIG. 3, and the length of the dilators 26 and the extent of the curvature is substantially uniform among the dilators. The probe members 20a-20f are arranged on the post 10 so that the dilators of the probe members are, advantageously, regularly graduated in size from one end of the post to the other. The probe members can, however, be arranged other than in graduated order without impeding the operability of the device.

As shown in FIGS. 3 and 4, the instrument includes means for maintaining the axial positioning of the probe members on the post. This means comprises an integral shoulder 32 formed on one end of the post, which shoulder is in engagement wit the outer end face 28 of the probe members 20f. Also, an annular groove 33 is formed in the post adjacent the other end thereof, and means 34 is mounted within the mounting portion 30 of the probe member 20a, which overlies and resiliently engages the annular groove. The resilient engagement is such that the probe member having the means for resiliently engaging the groove mounted therein may be removed from the post by applying an axial force thereto. This feature advantageously permits disassembly of all of the probe members from the post to facilitate cleaning and sterilization thereof. The widths of the mounting portions of the probe members and the position of the annular groove are selected so that each probe member, while able to freely rotate, is substantially stationary in axial position and does not slide up and down the post.

In the preferred embodiment, the means 34 for resiliently engaging the groove 33 comprises a ball detent. The ball detent comprises a bore 35 communicating between the transverse opening 24 and the cylindrical outer wall 30 of the mounting portion of a probe member. Preferably, and as illustrated, the ball detent is located in the mounting portion 22 of the probe member 20a and which has the greatest thickness of all the mounting portions of the probe members. A ball 36 is disposed in the bore 35. The bore has a lip 37 formed on the inner end thereof which prevents the ball from passing therethrough but permits the ball to partially project into the transverse opening 24 a distance sufficient to engage the annular groove 33. The ball is resiliently supported by a spring 38, and the spring held in place by a screw 39.

The invention has been described with a degree of specificity above. This description has been provided to illustrate the invention and is not to be taken as restrictive thereof, the scope of the invention being defined by the following claims. Equivalents of the claims ar to be included therein.

That which is claimed is:

1. A surgical instrument adapted to probe body orifices of different sizes, and comprising
   a post defining a central axis,
   a plurality of separate probe members mounted in a side-by-side arrangement axially along said post, and for independent rotation about said axis, with each of said probe members comprising a mounting portion having a transverse opening receiving said post, and an elongate dilator extending radially outwardly from said mounting portion, and with each dilator having a size different from that of the other dilators of said instrument, and with the probe members being configured such that each may be freely and independently rotated about said axis of said post without interference with other probe members, and
   means for maintaining the axial positioning of said probe members on said post,
   whereby a probe member having a dilator of a desired size may be selected and rotated to a position where such dilator is separated from the other dilators, to thereby permit the selected dilator to be individually used in probing a body orifice.

2. The surgical instrument as defined in claim 1 wherein the mounting portions of said probe members each are of a disc-like configuration and include opposite parallel end faces which lie in planes which are perpendicular to said central axis of said post.

3. The surgical instrument as defined in claim 2 wherein the adjacent end faces of adjacent mounting portions are in contact with each other, and wherein the mounting portions have cylindrical outer peripheral walls which extend coaxially about said axis of said post and which are of equal diameter.

4. The surgical instrument as defined in claim 3 wherein the elongate dilators are each arcuately curved along its length when viewed in a direction perpendicular to said central axis of said post, and with the length of the dilators and the extent of the curvature being substantially uniform among the dilators.

5. The surgical instrument as defined in claim 4 wherein there are at least four of said probe members, and said dilators of said probe members are regularly graduated in size from one end of said post toward the other.

6. The surgical instrument as defined in claim 2 wherein said means for maintaining the axial positioning of said probe members comprises an integral shoulder on one end of said post which is in engagement with the outer end face of one of the probe members, an annular groove in said post adjacent the other end thereof, and means mounted within the mounting portion of another one of said probe members which overlies said annular groove for resiliently engaging said groove, and such that said another one of said probe members may be removed from said post by applying an axial force thereto, so as to permit disassembly of all of said probe members from said post to facilitate cleaning thereof.

7. A surgical instrument adapted to probe body orifices of different sizes, and comprising
   a post defining a central axis,
   a plurality of separate probe members mounted in a side-by-side arrangement axially along said post and for independent rotation about said axis, with each of said probe members comprising a mounting portion having a transverse opening receiving said post, and an elongate cylindrical dilator extending radially outwardly from said mounting portion and tapering to a blunt point, wherein said elongate dilators are each arcuately curved along its length when viewed in a direction perpendicular to the axis of said post, with the length of the dilators and the extent of the curvature being substantially uniform among the dilators, and with each dilator having a size different from that of the other dilators of said instrument, each of said mounting portions of said probe members being of a disc-like configuration and including opposite parallel end faces which lie in planes which are perpendicular to said axis of said post, and with the thickness of each of said mounting portions between said parallel end faces being at least as great as the maximum diameter of said dilator so that each of said probe members may be freely and independently rotated about said axis of said post without interference with other probe members, and
   means for maintaining the axial positioning of said probe members on said post,
   whereby a probe member having a dilator of a desired size may be selected and rotated to a position where such dilator is separated from the other dilators, to thereby permit the selected dilator to be individually used in probing a body orifice.

8. The surgical instrument as defined in claim 7 wherein there are at least four of said probe members, and said dilators of said probe members are regularly graduated in size from one end of said post toward the other.

9. The surgical instrument as defined in claim 7 wherein said means for maintaining the axial positioning of said probe members comprises an integral shoulder on one end of said post which is in engagement with the outer end face of one of the probe members, an annular groove in said post adjacent the other end thereof, and means mounted within the mounting portion of another one of said probe members which overlies said annular groove for resiliently engaging said groove, and such that said another one of said probe members may be removed from said post by applying an axial force thereto, so as to permit disassembly of all of said probe members from said post to facilitate cleaning thereof.

* * * * *